United States Patent [19]
Allen et al.

[11] Patent Number: 6,126,615
[45] Date of Patent: Oct. 3, 2000

[54] SUTURELESS GUIDED SKIN BIOPSY SYSTEM

[76] Inventors: Michael E Allen, 234 E. Chickasaw Pkwy., Memphis, Tenn. 38111; E William Rosenberg, 6055 Sweetbriar Cove, Memphis, Tenn. 38120

[21] Appl. No.: 09/113,746

[22] Filed: Jul. 10, 1998

[51] Int. Cl.⁷ ..................................................... A61B 5/00
[52] U.S. Cl. ........................... 600/562; 606/172; 606/215
[58] Field of Search .................................. 606/218, 216, 606/220, 217, 219, 221, 215, 172; 600/562

[56] References Cited

U.S. PATENT DOCUMENTS

| | | | |
|---|---|---|---|
| 3,926,193 | 12/1975 | Hasson | 606/218 |
| 3,971,384 | 7/1976 | Hasson | 606/218 |
| 4,114,624 | 9/1978 | Haverstock | 606/167 |
| 4,192,312 | 3/1980 | Wilson | 606/1 |
| 4,576,163 | 3/1986 | Bliss | 606/1 |
| 4,815,468 | 3/1989 | Annand | 606/216 |
| 5,176,703 | 1/1993 | Peterson | 606/216 |
| 5,693,068 | 12/1997 | Kuhlman | 606/201 |

*Primary Examiner*—Cary O'Connor
*Assistant Examiner*—Pamela Wingood

[57] ABSTRACT

A skin biopsy system covers all aspects of the biopsy procedure from initial incision to final closure. The system includes a flexible closure consisting of 4 elongated rigid members interconnected by flexible hinges. The opening within the closure is initially diamond-shaped, approximating an ellipse, which is then deformed or pinched to a narrow linear opening when the wound is closed. Included with the system is a knife which interacts with the closure to yield a guided incision of constant depth. The path of the knife is guided by interference between the blade and the inside faces of the closure while the depth is limited by interference of the handle proximal the blade and the top faces of the closure.

5 Claims, 9 Drawing Sheets

SUTURELESS GUIDED SKIN BIOPSY SYSTEM

BACKGROUND

1. Field of Invention

The present invention relates generally to surgical instruments, and more particularly to a complete skin biopsy apparatus which first guides the path and depth of incision and then closes the wound without the use of sutures.

2. Discussion of Prior Art

As is well known in the art, it is often necessary to excise a sample of skin for further histologic study. Traditionally, this surgical procedure was performed "free-hand" by a surgeon using a scalpel. An incision was made about the lesion to create an island of skin that was then lifted by forceps to expose the underlying tissue. The underlying tissue was then cut away, such that the sample of skin could be removed. Finally, the wound was sutured.

Ideally, an elliptical incision of uniform depth was made (the depth was chosen according to skin thickness, as it relates to location on the human body). The elliptical shape and constant thickness of the wound allowed opposing sides of the wound to be drawn together with minimal stretching or distortion of the skin. The result was accelerated healing, and reduced visible scarring.

Further improved healing and reduced scarring could be realized by a pinching and an eversion of the wound upon closure. Pinching the wound together such that the surfaces brought into apposition tended to bunch and roll upward, imposed compressive stresses proximal to the wound that would balance the natural tendency of the wound to pull apart. This permitted the skin tissues near the seam to relax while maintaining adequate pressure within the seam itself. The result was a very thin scar. A wound that had not been so addressed would tend to pull apart at the seam during healing, relying on scar tissue to fill the wider gap. In addition, the rolling upward, or eversion of the skin tissue insured that the outermost layer, or epidermis would not interfere with healing. If epidermis were trapped in the wound, a valley-like scar could result.

While the biopsy procedure required only a few steps to complete, it was difficult for the surgeon to make an ideal incision that would form the basis for optimum healing upon closure. A good deal of skill was also required in closing the wound if all of the previously mentioned features where to be incorporated for optimum healing and minimal scarring. The problem of suture tracks, or scars left by the suture wounds, is a necessary drawback of sutured closures.

While solutions specific to the problem of making an accurate elliptical incision exist in the prior art, none of these inventions address closure of the wound. An example of such a solution is depicted in U.S. Pat. No. 5,183,053 issued to Yeh et al., which shows a biopsy punch with an elliptical blade. The Yeh invention seeks a solution to the problem of an accurate incision, but in no way does it address closure of the wound.

Alternatives to conventional sutures as a means of general wound closure (not biopsy wounds specifically) are suggested in the prior art as well. U.S. Pat. No. 5,176,703 issued to Peterson depicts a sutureless closure with a means for "mounding the flesh" together for the purpose of improved healing. This closure is appropriate only for generally elongate wounds, and not for biopsy wounds. The biopsy wound is elliptical in shape and would require a bandage that conforms to this shape. Furthermore, the size of the typical biopsy wound would require a bandage, or bandages, of such small size that manipulation of the wound and the dressing would be difficult. Finally, these general wound closures in no way serve as an aid to making the initial biopsy incision.

As evidenced by the prior art, there is a need for solutions to the problems and difficulties associated with the two primary aspects of the biopsy procedure, namely the aspect of achieving a proper incision, and the aspect of achieving a proper closure. No single prior art provides a comprehensive solution to all of the problems associated with the skin biopsy procedure.

A comprehensive yet simple solution that is economical and easy to use, would transform the current biopsy procedure into a 'kit' that would enable surgeons and non-surgeons alike to perform the perfect biopsy.

OBJECTS AND ADVANTAGES

The present invention is a complete system which provides an inexpensive and simple solution to the problems of obtaining an accurate elliptical incision of uniform proper depth, and a closure of the wound wherein the opposing tissue is brought together uniformly and in a manner that yields an eversion and mounding of the tissue at the seam.

It is a general object of the current invention to provide a comprehensive solution to all of the aforementioned problems related to the skin biopsy procedure.

It is a further object of the present invention to provide a device which acts first as a means of mechanically guiding the path of the incising knife, and secondly as a means of closing the wound without the use of sutures.

It is a further object of the present invention to provide a means of maintaining the incising blade at a constant cutting depth relative to the surface of the skin.

It is a further object of the present invention to provide an adjustable depth of cut.

It is still another object of the invention to guide the path of the incising knife along a boundary which closely approximates an ellipse.

It is yet another object of the present invention to provide a closure which pinches the wound closed and under pressure so as to promote healing.

It is another object of the present invention to insure accurate alignment of the edges of the wound upon closure so as to minimize scarring.

It is still another object of the present invention to evert the edges of the wound upon closure so as to minimize scarring.

The system is simple and cost effective, such that the entire system is disposed of after use.

Further objects and advantages of the invention will become apparent from a consideration of the drawings and ensuing description.

SUMMARY

Accordingly, the reader will see that the apparatus of the present invention provides a complete and simple system for performing a skin biopsy procedure. The apparatus yields an optimal tissue sample by mechanically guiding the knife along a bisymmetrical path approximating an ellipse. At the same time, the depth of cut is also maintained at a constant, but adjustable depth to provide a tissue sample of uniform thickness. Finally, the apparatus yields ideal healing conditions by drawing the wound closed evenly and under pressure and in a manner which causes an eversion of the opposing tissues of the wound.

DETAILED DESCRIPTION OF THE PREFERRED EMBODIMENTS

Figure 1A:
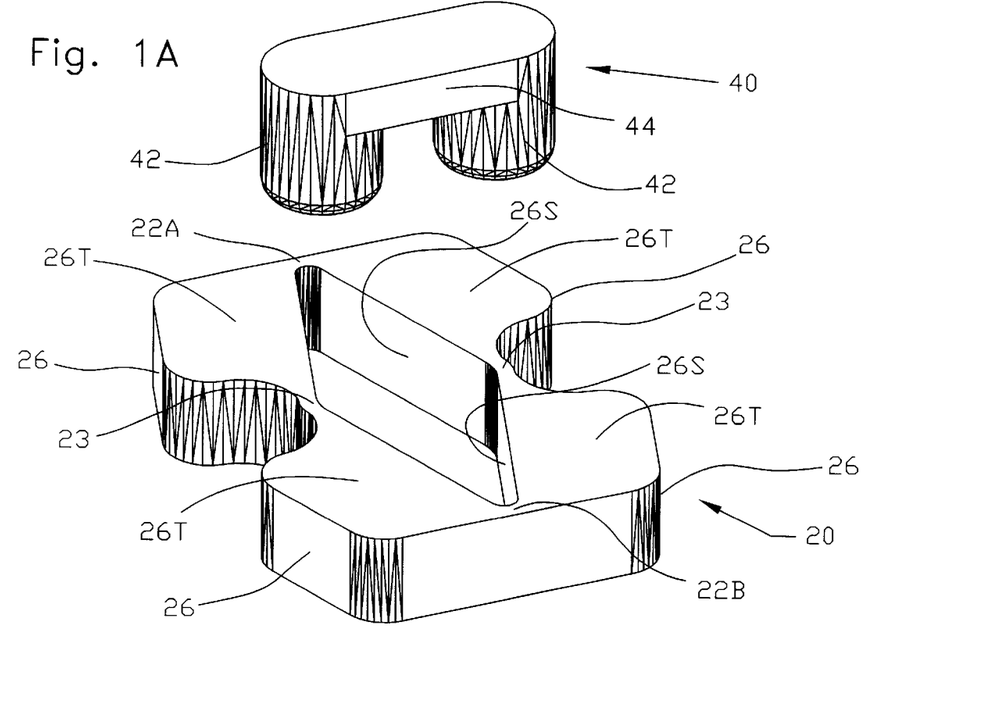
FIG. 1A is a perspective view of the primary component of a first embodiment of the present invention in its natural configuration or molded shape.

A preferred embodiment of the primary component of the present invention is illustrated in FIG. 1A. A closure 20 is depicted in its naturally open or "as molded" configuration and is comprised of four interconnected legs 26 joined at the ends by thin sections forming the hinges 22a, 22b, and pair of hinges, 23. Each of legs 26 is identical in every dimension. Indicated in cross-section in FIG. 11, the bottoms 26B of legs 26 are molded with a slight grade rising towards the center of the closure. Attached to bottoms 26B of legs 26 is a sheet of backing paper shown partially peeled back in FIG. 4, but not present in FIG. 11 since it would have been removed in an earlier stage of the biopsy procedure. The backing paper initially protects a layer of adhesive, coating bottoms 26B. Adjacent faces of legs 26, except for bottoms 26B previously discussed, are orthogonal to one another. Hinges 28 are molded integral with legs 26, but of a thickness that permits flexing without breaking. The resulting configuration is a parallelogram closely approximating an ellipse.

FIG. 1A further depicts clip or clevis 40 positioned directly above closure 20. Clevis 40 comprises a pair of posts 42 connected by a bridge 44.

Figure 1B:
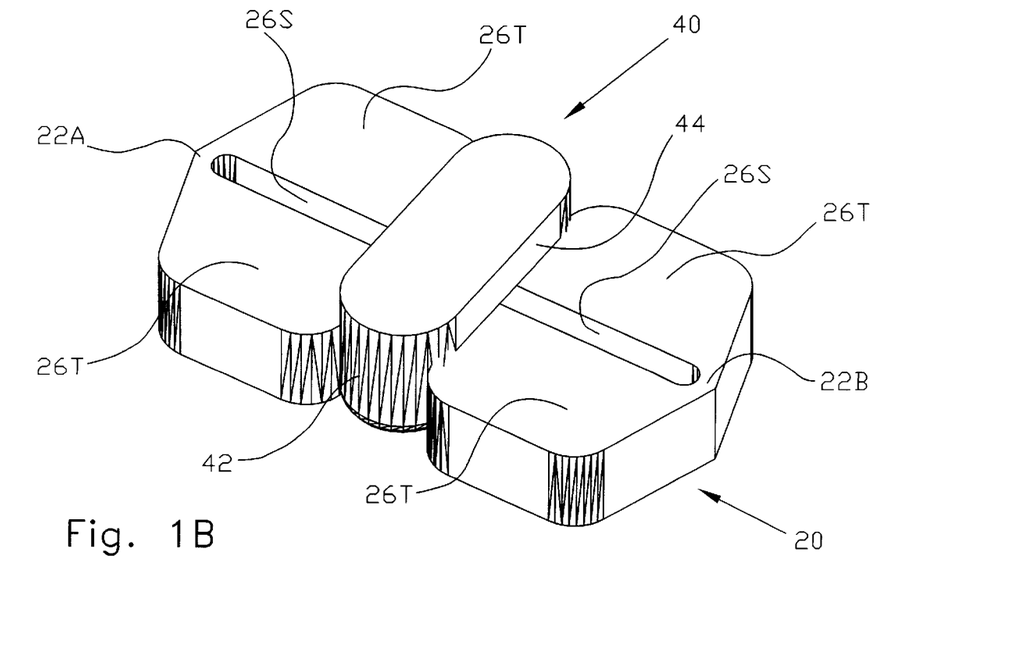
FIG. 1B is a perspective view of the component of FIG. 1A depicted in its deformed or closed state.

FIG. 1B shows closure 20 in its deformed or closed state as it would appear following the biopsy procedure. Clevis 40 has been assembled to closure 20 via a friction fit between posts 42 and a pair of receptacles at hinges 23 which are formed only once closure 20 has been deformed into its closed state.

Figure 2:
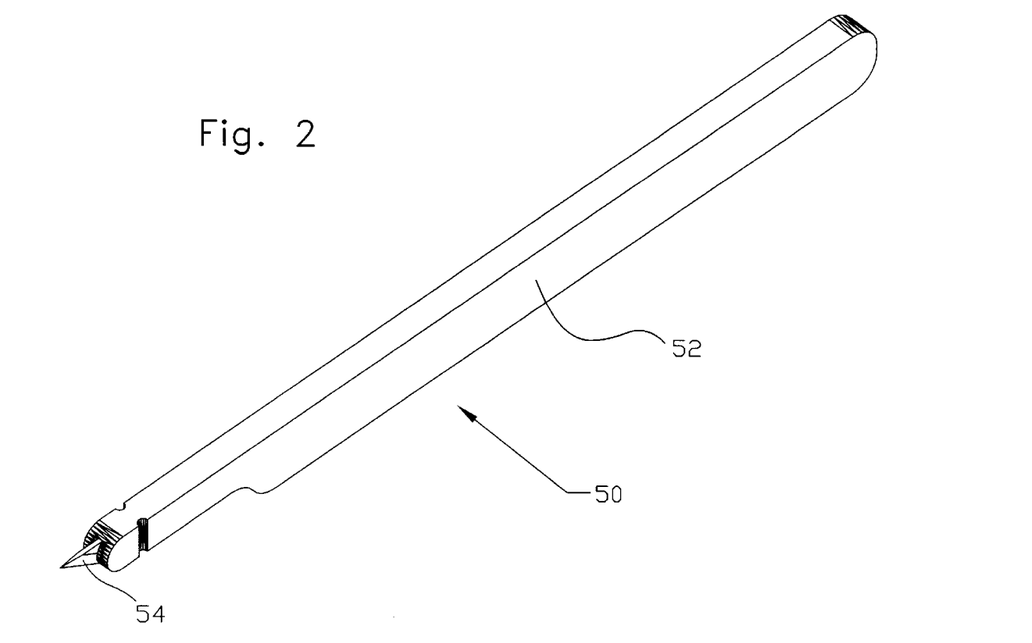
FIG. 2 is a perspective view of a knife constructed in accordance with the present invention.

FIG. 2 depicts a typical embodiment of a secondary component constructed in accordance with the present invention. A surgical knife 50 comprises a blade 54 insert molded with a handle 52.

Figure 3:
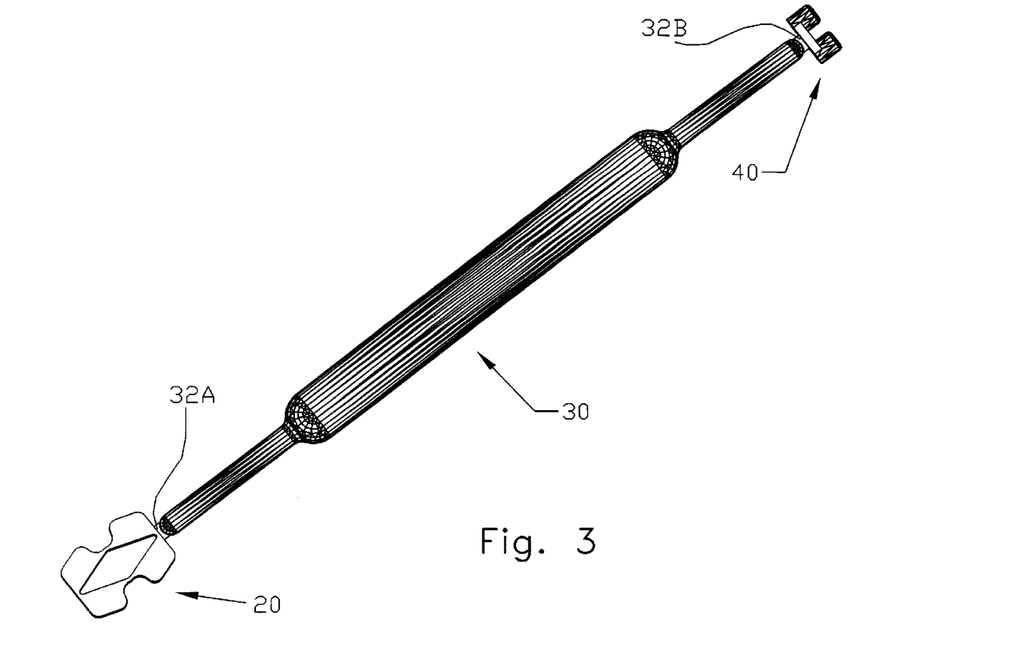
FIG. 3 is a perspective view of the various molded components constructed in accordance with the present invention.

FIGS. 2 and 3 together further illustrate all the components of the present invention as they might be packaged for distribution. All components shown, excluding only blade 54, are injection molded from a flexible plastic such as nylon. A tool 30 is a sprue resulting from the molding process and connects at one end to closure 20 through gate 32a and at its opposite end to clevis 40 through gate 32b.

OPERATION OF INVENTION

Figures 4, 5:
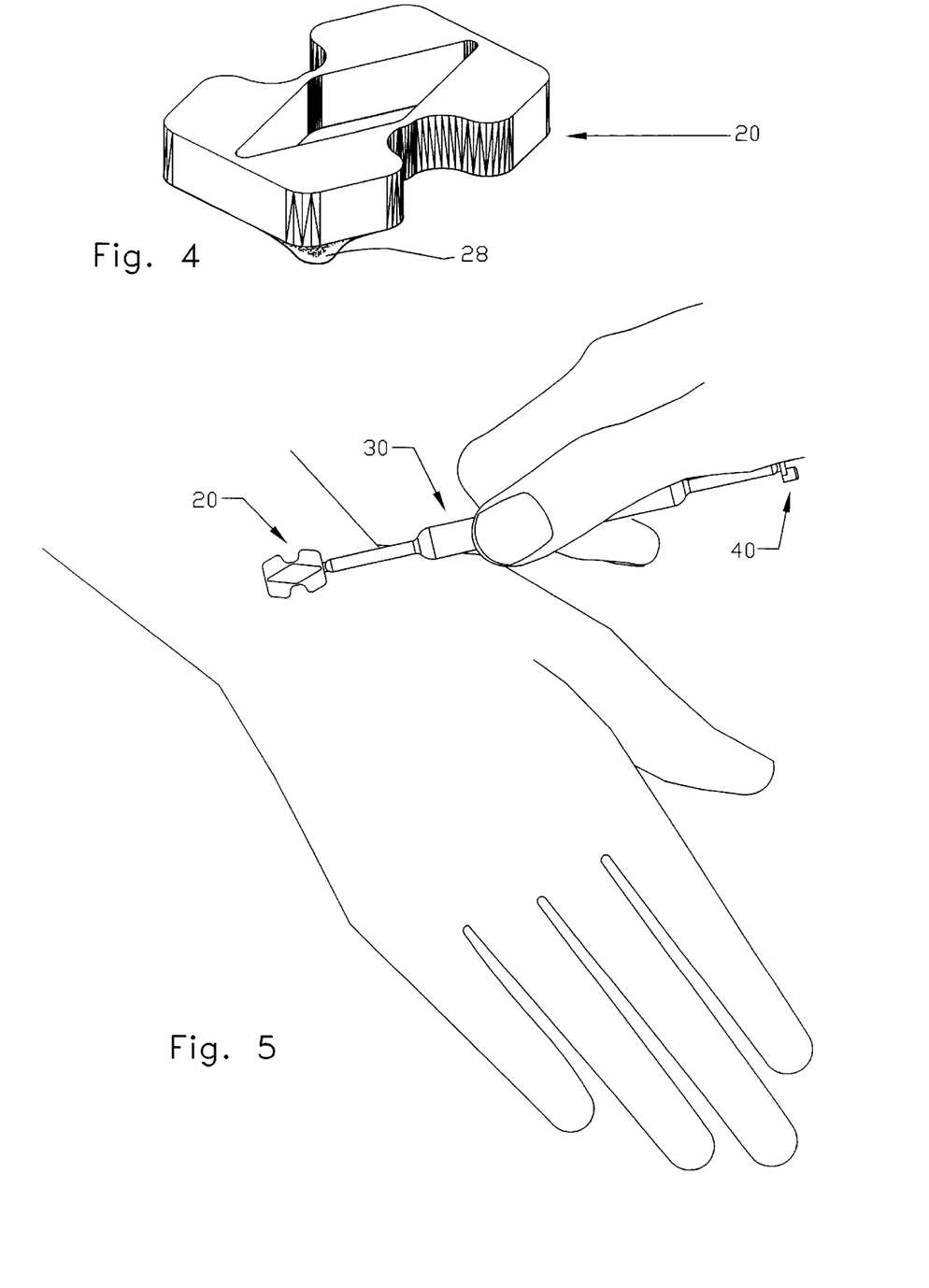
FIG. 4 is a perspective view of a primary device showing an adhesive backing paper partially removed
FIG. 5 is a perspective view of a primary device being applied to the arm of a patient.

The present invention and its components comprise a complete system aiding in the performance of a typical skin biopsy procedure. Referring to FIG. 5, the invention is used by taking in hand tool 30, which has connected to it at one end closure 20. The free hand peels away a backing paper 29, depicted in FIG. 4, from bottoms 26b of legs 26 thereby exposing a layer of adhesive. Tool 30 is used to manipulate closure 20 to a position directly above the area to be sampled, and bottoms of legs 26 are then brought into contact with the surrounding skin. A finger of the other hand (not shown) is pressed firmly against top 26t to insure complete contact between the bottom of closure 20 and the skin surface. Once the adhesive has set, a finger continues to press closure 20 to the skin while tool 30 is rotated through 90 degrees, thereby twisting and fracturing gate 32a and separating tool 30 from closure 20. Tool 30 is then set aside. Closure 20 is now affixed to the patient's forearm thereby surrounding the lesion and defining the area to be cut.

Figure 6A:
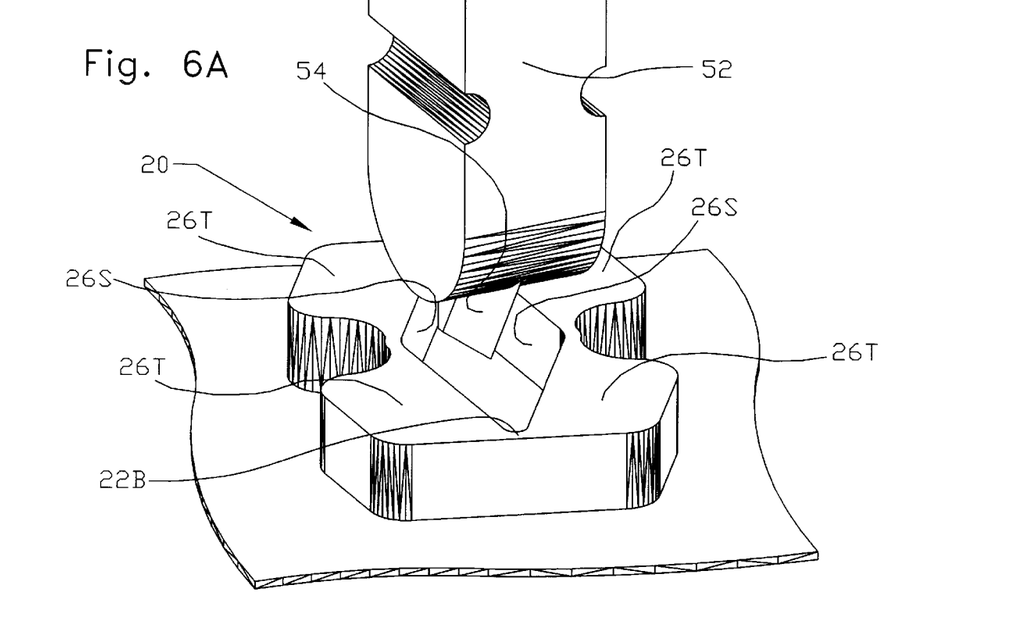
FIGS. 6A and 6B are two differing views of the same initial incision.
Figure 6B:
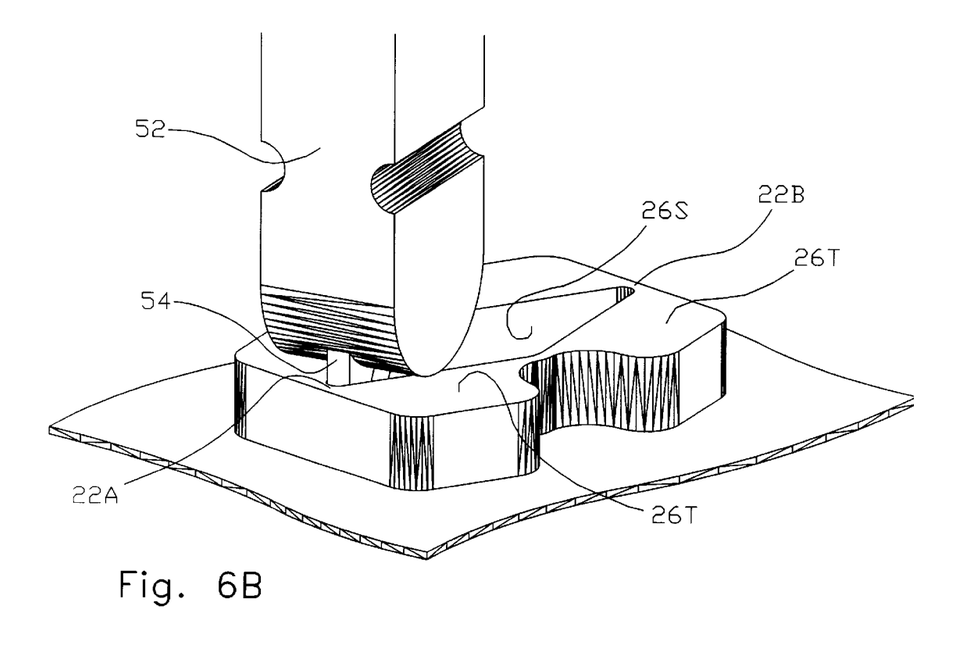
Figure 7:
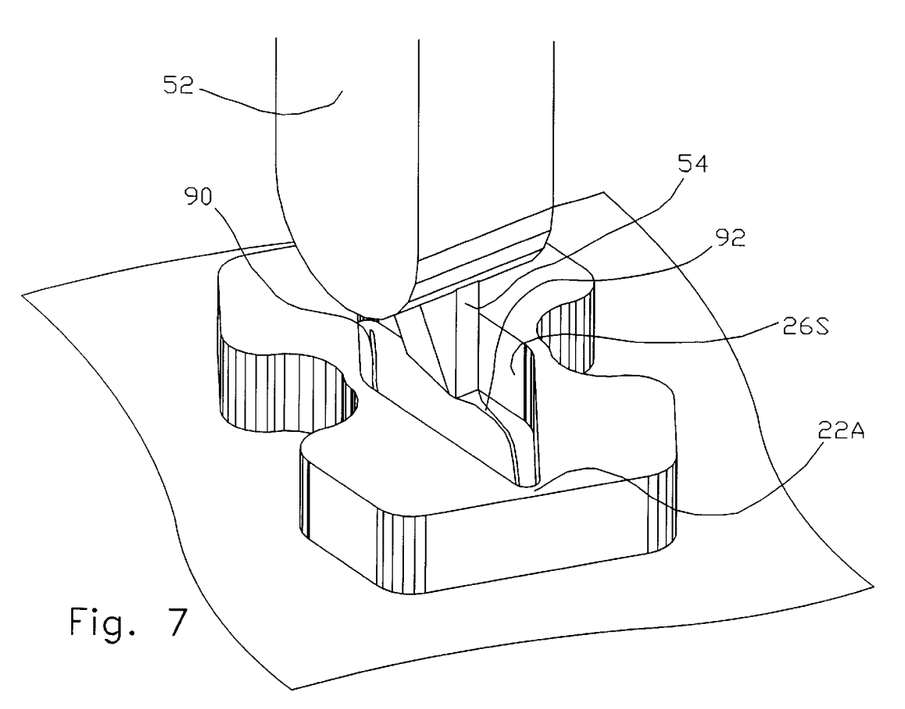
FIG. 7 is a perspective view of the final incision.
Figure 8:
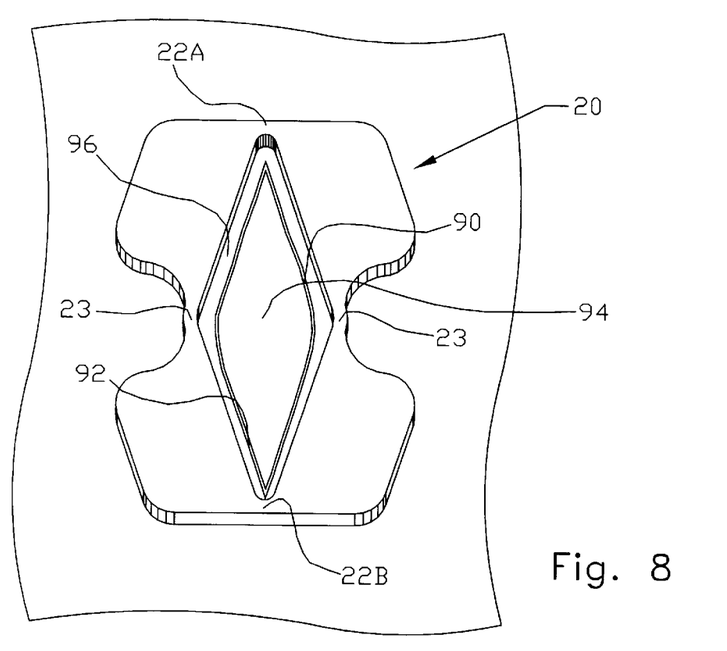
FIG. 8 is a perspective view of the completed incision with the blade removed. The elliptical island of tissue is still present.

Knife 50 is then taken in hand in preparation for the initial incision. FIGS. 6A and 6B are two different views of the same initial incision. The tip of blade 54 is located interior to the closure at hinge 22a. One of the sides of blade 54 should contact inner side 26s of closure 20. Downward pressure is applied to handle 52, forcing blade 54 to sever the skin. The blade will sink to a depth limited by the contact of handle 52 as shown in FIGS. 6A and 6B. Knife 50 is then drawn toward the user while maintaining contact between the side of blade 54 and inner side 26s, and between the handle 52 and the surface of top 26t. Once blade 54 reaches hinge 22b, blade 54 is lifted out of the skin and returned to the same location where began the first incision. This time, the opposite side of blade 54 is made to contact inner side 26s of leg 26 opposite the first leg used to guide knife 50. Again the blade is forced into the skin and limited to a depth determined by contact of handle 52 with the surface of top 26t. Knife 50 is again drawn toward the user while maintaining contact with both inner side 26s and top 26t. FIG. 7 shows completion of the second and final incision. Knife 50 is then withdrawn, leaving a pair of incisions which together approximate an ellipse (FIG. 8). It should be noted that the shape of the incision depicted in FIG. 8 is supported by trials involving pigs feet, where the knife did indeed leave the highly desirable elliptically shaped incision as the blade could not follow the small radii at hinges 23 and instead rounded these areas.

A forceps (not included in the apparatus) is used to grab the elliptical island of tissue and lift it to expose the underlying connecting tissue. Knife 50 is used to cut away this connecting tissue. Knife 50 can now be discarded.

Figure 11:
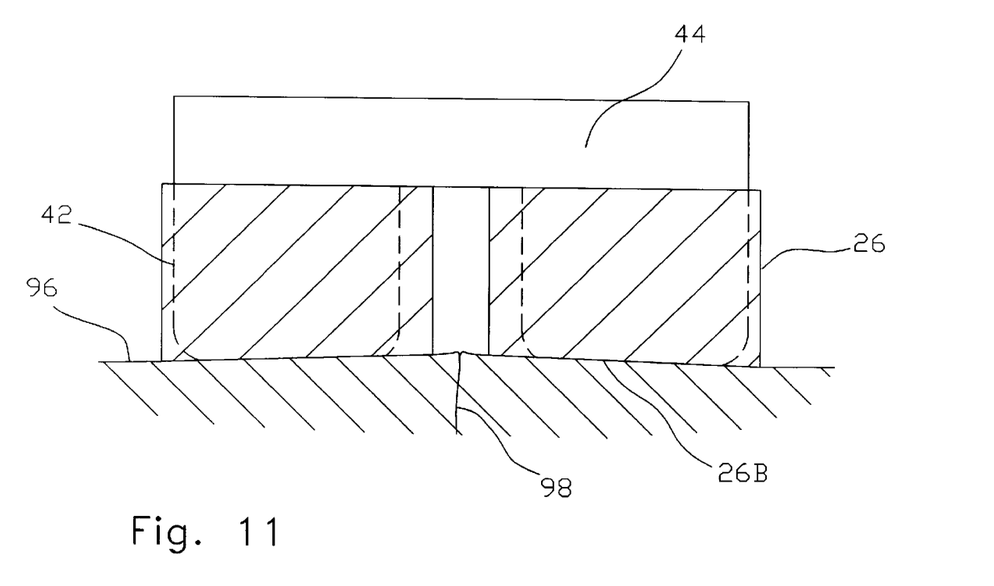
FIG. 11 is a sectional view of a primary device in its closed state, adhered to the patient's skin.

What is left is an elliptical wound, bounded by closure 20 adhered to the tissue proximal to the wound. A margin of tissue 96, visible in FIG. 8, resides between legs 26 and the edges of the wound. This margin of tissue insures that the opposing edges of the wound will be in compression once closure 20 has been deformed and locked in its closed configuration (FIG. 11).

Figure 9:
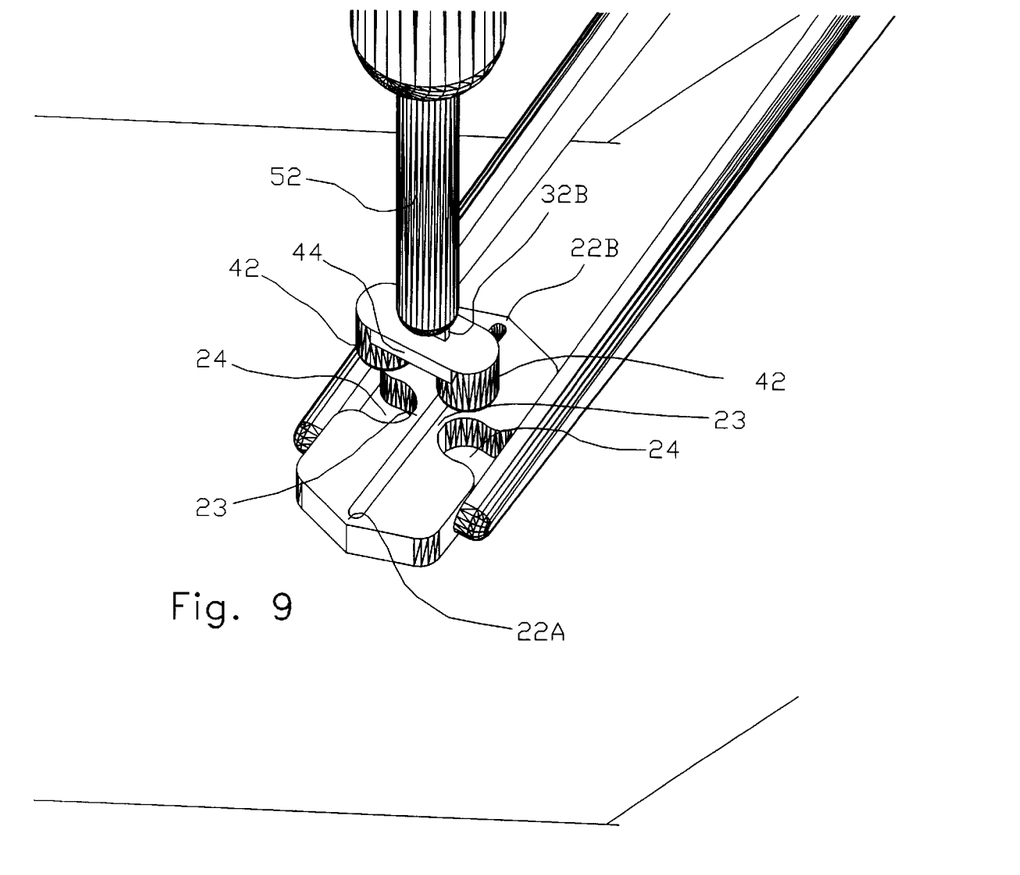
FIG. 9 is a perspective view of a primary device being pinched closed by forceps.
Figure 10:
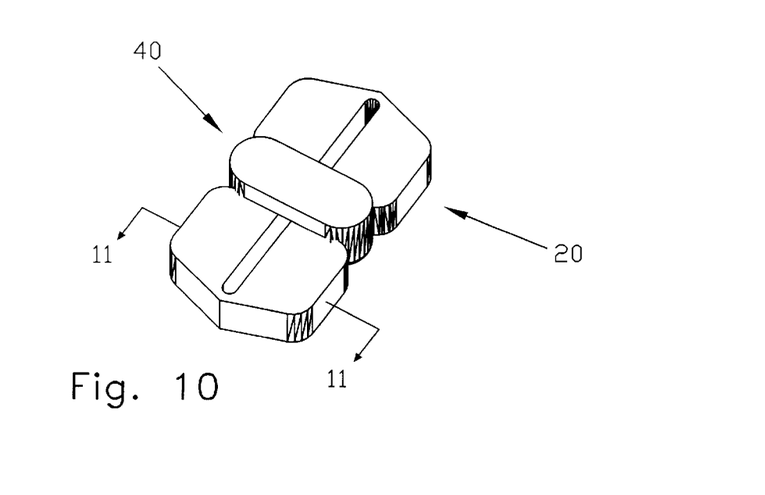
FIG. 10 is a perspective view of a primary device secured shut by installation of a clevis, as it would appear immediately following the completed biopsy procedure.

The forceps is then used to pinch closure 20 shut by placing the forceps about closure 20 so that the forceps contact the outer sides of opposing legs 26. With closure 20 held shut by the forceps, as shown in FIG. 9, tool 30 is taken in hand again, but this time tool 30 is oriented such that clevis 40 may be manipulated to interact with closure 20. Posts 42 of clevis 40 are positioned immeditately above hinges 23, and directed straight down such that posts 42 engage hinges 23. Hinges 23 form receptacles when closure 20 is in its closed state, and provide an interference fit for posts 42 of clevis 40. Clevis 40 is fully engaged once bridge 44 contacts top 26t of closure 20. Again tool 30 is rotated through 90 degrees, thereby fracturing gate 32b and separating tool 30 from clevis 40. Tool 30 can now be discarded. FIG. 10 depicts closure 20 as it will remain on the patient until it falls away naturally due to the normal shedding of skin.

A strip of colored tape may be placed over closure 20 to hide it from view, and the procedure is complete. The device will fall off naturally after a time sufficient for the wound to heal. No sutures need be removed. No additional consultation should be necessary.

DIMENSIONS

Regarding the dimensions of closure 20, the device should be of a height or thickness that will provide a rigid guide for the blade of a scalpel, but thin enough that the device does not become obtrusive. The preferred embodiments indicate a closure that is approximately 2 mm in height, but other embodiments may require thickness ranging from near 0 to heights greater than 2 mm. If closure 20 must be adhered to a rapidly changing surface, the thickness of closure 20 should be such that it will conform to the surface through bending. Additionally, a more flexible material could be used depending on the requirements. The width of legs 26 of closure 20 are shown to be approximately 4 mm across at their widest sections. This width was chosen to provide ample support for knife 50, as well as sufficient surface area for adherence to the skin. Additional embodiments may call for a leg width ranging from 1 mm to 8 mm. The aforementioned gradient of bottoms 26b of legs 26 is included to insure that the edges of the wound will be predisposed to roll upward once closure 20 is pinched closed and the edges of the wound are forced to bunch under compression; the highly desired eversion is realized as illustrated in FIG. 20. The gradient may range from 1–5 degrees; a 2 degree slope is illustrated in FIG. 20. Hinges 22a, 22b should be molded to dimensions that will yield cylindrical receptacles of a diameter slightly less than the diameter of posts 42 of clevis 40. The interference fit will insure that clevis 40 remains in place and further insure that closure 20 will remain rigidly fixed or locked in position, tending neither to open nor close. The embodiment described herein suggests a receptacle diameter of 3.1 mm (0.123 in) and a post diameter of 3.2 mm (0.125 in). Finally, the length of legs 26, which determine the size and shape of the elliptical opening or enclosed area defined by closure 20, should be sized to yield a major axis to minor axis ratio of 3 to 1. Therefore, for a closure 20 that is designed to obtain a typical 4 mm sample, the device should be constructed so that the distance between hinges 23 is somewhat larger than 4 mm while the distance between hinges 22a and 22b is just over 12 mm. The additional allowance accounts for the margin of tissue left behind as a result of the nonzero thickness of blade 54. The cutting edge of blade 54 is offset from legs 26 by a distance equal to one half the thickness of blade 54. The design of closure 20 allows for further adjustment of the shape of the incision, since closure 20 can be easily deformed before applying it to the skin.

Regarding the dimensions of clevis 40, the diameter of posts 42 are determined in relation to the receptacles of closure 20 formed at hinges 23 when closure 20 is in its deformed state. As previously mentioned, the preferred embodiment describes posts 42 having diameter 3.2 mm (0.125 in). Furthermore, the length that posts 42 extend from the bottom of bridge 44 is limited by the thickness of closure 20. If posts 42 extend beyond the bottom of closure 20, posts 42 will interfere with the surface of the skin. Bridge 44 should be of a width equal to the diameter of posts 42 and have a thickness of approximately 0.8 mm (0.030 in). The ends of posts 42 are filleted to help guide posts 42 into the receptacles at hinges 23 of closure 20.

Regarding the dimensions of knife 50, handle 52 should be of a length that is easy to manipulate. Handle 52 should also be wide enough to interact with and be supported by top 26t of closure 20, but not so wide that it inhibits the user's view of the working area. Blade 54 should extend from handle 52 a distance equal to the sum of the thickness of closure 20 and the depth of cut required. The simplicity of knife 50 and its low cost of manufacture makes feasible the inclusion of multiple knives 50 that differ only in depth of cut. For a lesion located anywhere on the body, one of two depths of cut will be appropriate. Therefore, at most two knives would be included in a package for distribution.

ADDITIONAL EMBODIMENTS

Figure 14A:
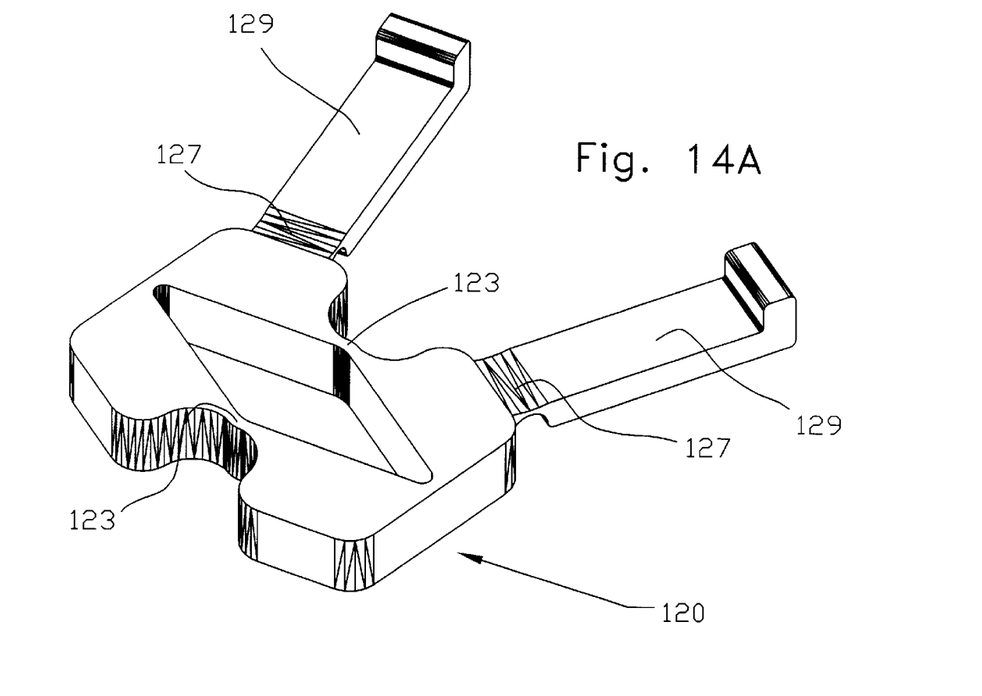
FIGS. 14A and 14B are perspective views of the primary component of a second embodiment of the present invention.
Figure 14B:
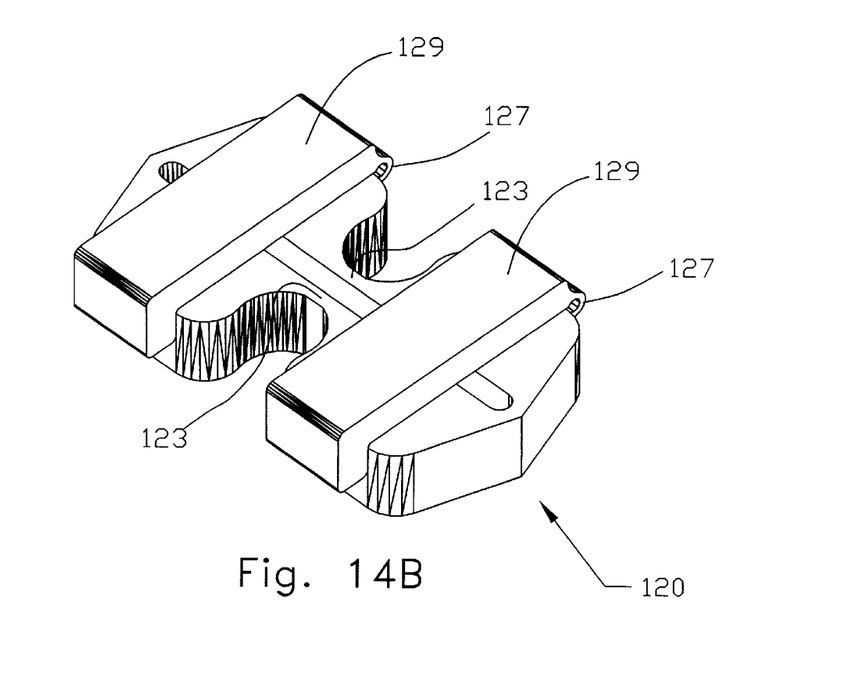

A second embodiment of the primary component of the present invention is illustrated in FIGS. 14A and 14B. Closure 120 is identical to closure 20 of the first embodiment depicted in FIGS. 1A and 1B, except for the addition of clips 127 molded integral with closure 120 and connected near the top of closure 120 by thinned sections or clip hinges 129. It should be noted that closure 120 can be easily closed by placing the tips of the forceps over hinges 123 and pinching shut. In this case, the receptacles at hinges 123 provide clearance for the forceps to be withdrawn once clips 127 have been folded into position.

FIG. 14B shows closure 120 of the second embodiment in its deformed or closed state as it would appear following the biopsy procedure. Clips 127 have been folded over the top to retain closure 120 in its closed state.

Figure 12:
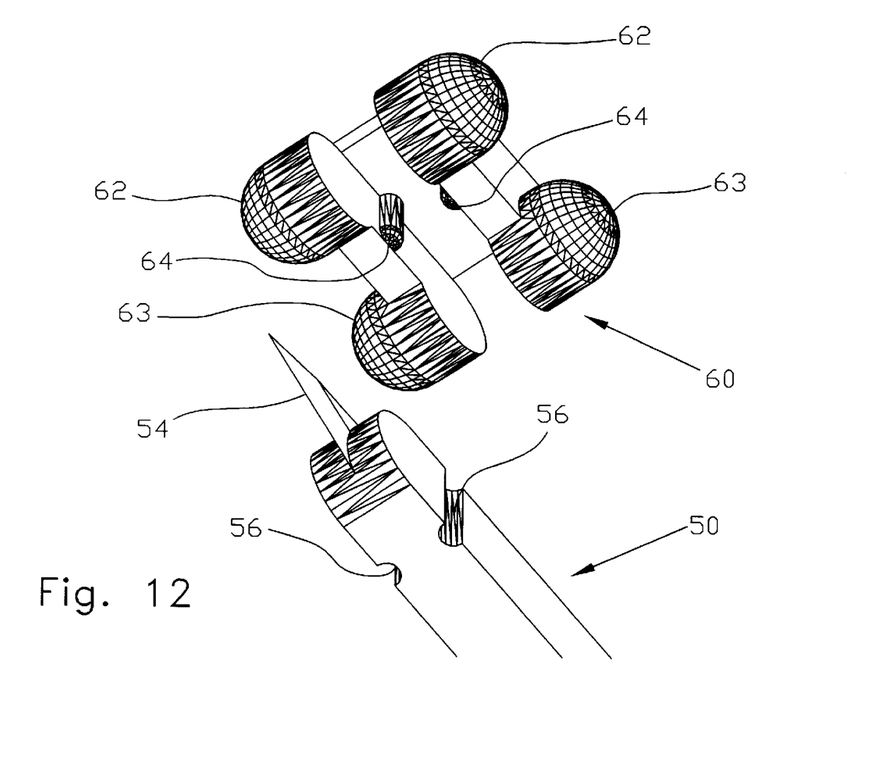
FIG. 12 is a perspective view of a second embodiment of a secondary component (knife) of the present invention, which includes an attachable depth limiting guard.
Figure 13A:
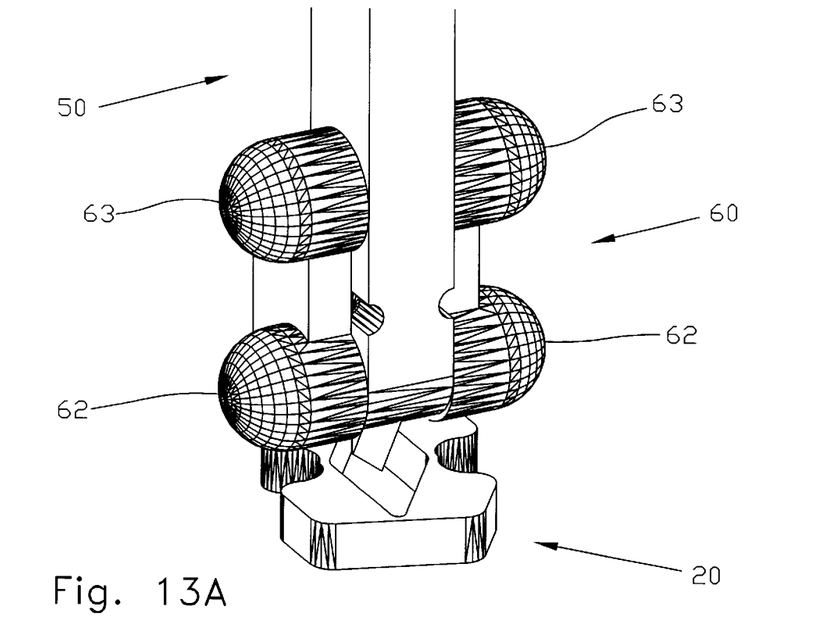
FIGS. 13A and 13B are two differing views of the same initial incision of FIGS. 6A and 6B with the addition of a depth-limiting device applied to the knife.
Figure 13B:
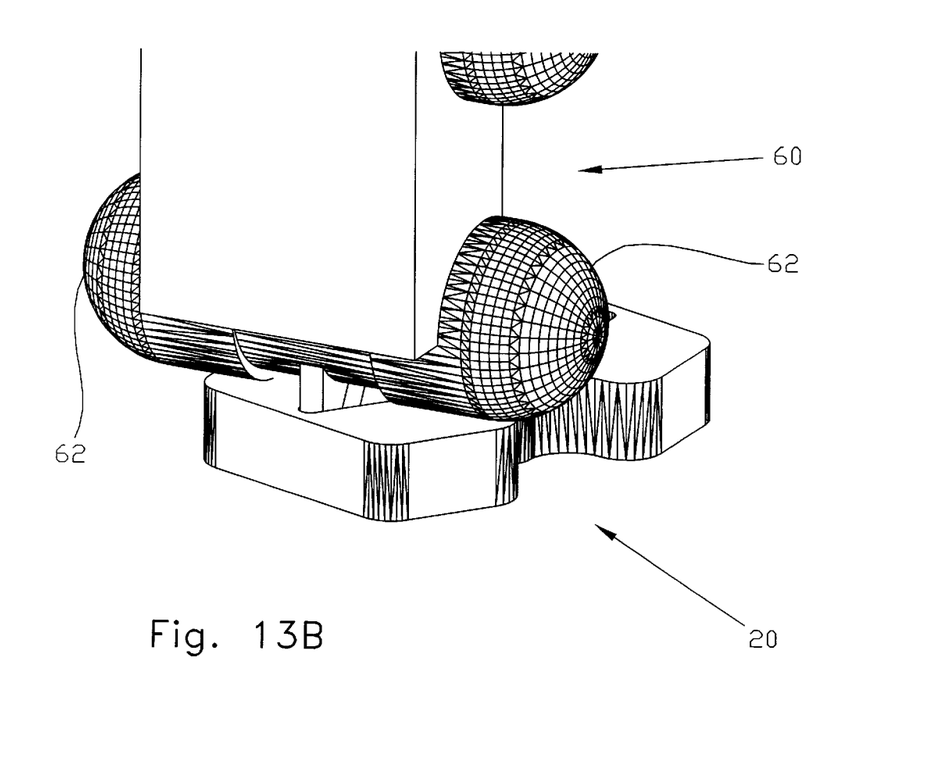

FIG. 12 illustrates a second embodiment of the knife of the present invention. A limiter 60 is added to yield a knife that has an adjustable depth of cut. One of two depths is chosen by orienting limiter 60 in one of two possible directions. Limiter 60 is symmetric along both the vertical and horizontal axes except for a pair of locating rails 64 which are located slightly closer to pair of contacts 62 than to pair of contacts 63. The offset location of rails 64 enables a selection from two possible depths. Limiter 60 is attached to handle 52 via a friction fit or positive snap fit. Rails 64 always engage slots 56, but the location of limiter 60 will vary along handle 52. FIGS. 13A and 13B show limiter 60 installed with contacts 62 closer to blade 54, this positions limiter 60 further from blade 54. If instead, limiter 60 is installed with contacts 63 closer to blade 54, limiter 60 will be closer to blade 54. Therefore, with limiter 60 installed as shown in FIGS. 13A and 13B, the depth of incision has been chosen to be the deeper of the two possibilities. [It should be understood that if locating rails 64 where positioned an equal distance from either of contacts 62 or 63, then limiter 60 would not change position along handle 52 regardless of the orientation of limiter 60. Furthermore, the magnitude of the difference of the positions of limiter 60 is equal to twice the distance by which locating rails 64 are offset from center. Therefore if the selectable depths of cut differ by 2 mm, then locating rails 64 should be molded 1 mm closer to one of pairs of contacts 62 or 63 of limiter 60 than the other.]

It should be apparent that the closure of the present invention can be used with commonly available scalpels, and therefore packaged alone. In the case of using a more general scalpel, the depth limiting mechanism may not apply. The closure of the present invention could be constructed to an appropriate thickness such that the blade of the scalpel will be limited to the correct depth by interference of the handle of the scalpel with the top of the closure. Under these conditions, closure 20 might be packaged and designated for use with certain of the more popular scalpels in use.

CONCLUSIONS, RAMIFICATIONS AND SCOPE OF INVENTION

Accordingly, the reader will see that the present invention is a foolproof solution to perform all of the steps of a biopsy procedure beginning with the initial incision and finishing with final closure. Not only is it simple to use, requiring minimal training if any, but the path and depth guiding features coupled with the everting feature insures optimal wound closure and healing and a biopsy sample of uniform thickness and shape. Of major significance is the fact that the use of the present invention requires only minimal training of the operator, permitting those without the experience and skill of a surgeon to perform skin biopsies. Also worth reiterating is the low-cost and ease of manufacturing the components of the present invention, all of which (except for the small blade—possibly taken from a razor blade fragment) are injection molded from a very small quantity of plastic. Furthermore, as can be seen from the specification, the present invention provides the following advantages over the traditional methods of skin biopsy:

Many skin biopsies are made free-hand using a surgical blade on a permanent or disposable handle. This method requires both experience and skill to achieve an easily closable wound of uniform depth. Alternatively, the present invention allows a less experienced operator to achieve uniformly elliptical wounds of constant depth.

Another present method is that of using a round punch instrument to obtain a biopsy specimen. The resulting defect is more difficult to close than an elliptical shaped wound and is less likely to heal with an inconspicuous linear scar ("dog ears" typically result).

Present skin biopsies must be sutured closed. Suturing requires both skill and experience; the present invention does not make use of sutures to close the wound. In addition, sutures provide additional opportunity for scarring, known in the art as suture tracks—a row of small, dot-like scars appearing on either side of the wound. Sutures may also provide a focus for wound infection. Another drawback to the use of sutures is the requirement of an additional visit to the surgeon's office for removal of the sutures, with attendant costs of both the patient's and the surgeon's time. The present invention does not require such removal; the normal shedding of the skin at the edge of the wound carries the adhered device away. The time of such shedding of glued-on plastic is about one week; an appropriate period for wound healing.

Present skin biopsy practice often requires the use of a scalpel, forceps, needle-holder, suture on a needle, and scissors; only a forceps is required to accompany the present invention.

Present skin biopsy practice often requires a skilled operator and at least several minutes of time; the present invention can be successfully used by inexperienced operators such as generalist primary care providers after only minimal practice. The time required for use of the invention is less than is needed for a conventional biopsy method.

Thus, savings of time and equipment will provide economies in the provision of skin biopsy services.

While the preferred embodiments described in the specification are for a simple elliptical excision of a small sample skin biopsy, the principles described herein can be readily seen to be applicable to the surgical removal of larger skin lesions. Additionally, the invention could be used as a simple closure for wounds other than those resulting from biopsy.

It should be apparent from the various embodiments described herein, that many other variations of the present invention are possible. Accordingly, the scope of the invention should be determined not by the embodiments illustrated, but by the appended claims and their legal equivalents.

What is claimed is:

1. A skin biopsy guide and sutureless closure device which aids in both excising a biopsy specimen of the proper shape and thickness and which further aids in closing the resulting wound with minimal scarring and without the use of sutures, the device comprising:

an articulated parallelogram shaped enclosure comprised of multiple rigid members of equal length and substantially rectangular in cross section, each of said members hinged end-to-end in the plane of the enclosure, said hinges formed as thinned sections molded integral and continuous with said rigid members, the enclosure being collapsible by virtue of said hinges such that once the tissue specimen has been excised, the enclosure surrounding the elliptical shaped wound may deform in the plane of said enclosure from its original parallelogram shape to a collapsed configuration thereby closing said wound and whereby each of two pairs of opposing said rigid members lie parallel and proximal to said closed wound;

a clevis or clip which positively engages said enclosure at receptacles formed at two of said hinges when said enclosure is in its collapsed configuration, thereby retaining said enclosure in a closed state.

2. The enclosure of claim 1, whereby the thickness of said rigid members is sufficient to restrict the excising instrument to an elliptical path by interference with inside surfaces of said rigid members when the enclosure is in its undeformed configuration.

3. The enclosure of claim 1, wherein the bottom surfaces of said rigid members are molded with a slight grade rising toward the center of the enclosure.

4. The enclosure of claim 1, having an adhesive layer applied to bottom surfaces of said rigid members, said layer protected by a removable backing.

5. A skin biopsy and sutureless closure device, comprising:

an enclosure formed from four substantially rigid elongated members of equal length and substantially rectangular in cross-section, each of said rigid members connected end-to-end in the plane of the enclosure to another by thinned sections molded integral and continuous with said rigid members, said thinned sections form flexible hinges at each of four corners of said enclosure, the enclosure defining an open center portion extending therethrough;

a clip molded integral with one of said rigid members such that it may be folded over said enclosure, once said enclosure is in its deformed or closed configuration, thereby retaining said enclosure in a closed state.

* * * * *